United States Patent
Skulachev et al.

(10) Patent No.: US 9,427,444 B2
(45) Date of Patent: Aug. 30, 2016

(54) PHARMACEUTICAL AND COSMETIC COMPOSITIONS FOR ACCELERATED HEALING OF WOUNDS AND OTHER SURFACE DAMAGES

(75) Inventors: Vladimir P. Skulachev, Moscow (RU); Maxim V. Skulachev, Moscow (RU)

(73) Assignee: MITOTECH SA, Luxembourg (LU)

( * ) Notice: Subject to any disclaimer, the term of this patent is extended or adjusted under 35 U.S.C. 154(b) by 1537 days.

(21) Appl. No.: 12/524,972

(22) PCT Filed: Jan. 29, 2007

(86) PCT No.: PCT/RU2007/000043
§ 371 (c)(1),
(2), (4) Date: Aug. 3, 2010

(87) PCT Pub. No.: WO2008/094061
PCT Pub. Date: Aug. 7, 2008

(65) Prior Publication Data
US 2010/0292625 A1   Nov. 18, 2010

(51) Int. Cl.
| | | |
|---|---|---|
| *A61Q 17/00* | (2006.01) |
| *A61K 31/66* | (2006.01) |
| *A61K 8/55* | (2006.01) |
| *A61L 15/44* | (2006.01) |
| *A61L 27/54* | (2006.01) |
| *A61Q 19/00* | (2006.01) |
| *A61Q 19/08* | (2006.01) |

(52) U.S. Cl.
CPC . *A61K 31/66* (2013.01); *A61K 8/55* (2013.01); *A61L 15/44* (2013.01); *A61L 27/54* (2013.01); *A61Q 19/004* (2013.01); *A61Q 19/08* (2013.01); *A61K 2800/522* (2013.01); *A61L 2300/214* (2013.01); *A61L 2300/25* (2013.01); *A61L 2300/41* (2013.01)

(58) Field of Classification Search
CPC ..................................................... A61Q 17/00
See application file for complete search history.

(56) References Cited

U.S. PATENT DOCUMENTS

| | | | |
|---|---|---|---|
| 5,538,974 A | 7/1996 | Ogawa et al. | |
| 6,331,532 B1 | 12/2001 | Murphy et al. | |
| 7,109,189 B2 | 9/2006 | Murphy et al. | |
| 2002/0044913 A1* | 4/2002 | Hamilton | 424/59 |

(Continued)

FOREIGN PATENT DOCUMENTS

| | | |
|---|---|---|
| EP | 1047701 B1 | 5/2005 |
| EP | 1534720 A1 | 6/2005 |

(Continued)

OTHER PUBLICATIONS

Giorgini et al (Free Rad. Res., vol. 35, pp. 63-72, 2001).*

(Continued)

*Primary Examiner* — Benjamin Packard
(74) *Attorney, Agent, or Firm* — Wayne A. Keown; Verrill Dana LLP

(57) ABSTRACT

This invention relates to biology and medicine and in particular it can be used in medicine for preparation of pharmaceutical composition that can accelerate wound healing by means of directed transport of biologically active substances (bioactive compounds) to the mitochondria, using hydrogen electrochemical potential in mitochondria. Besides, this invention relates to a certain method of influencing on the organism by means of said directed transport of required biologically active substances.

4 Claims, 4 Drawing Sheets

(56) References Cited

U.S. PATENT DOCUMENTS

| | | |
|---|---|---|
| 2005/0065099 A1 | 3/2005 | Walkinshaw et al. |
| 2007/0259908 A1 | 11/2007 | Fujii et al. |
| 2007/0270381 A1 | 11/2007 | Murphy et al. |
| 2008/0275005 A1 | 11/2008 | Murphy et al. |

FOREIGN PATENT DOCUMENTS

| | | |
|---|---|---|
| EP | 1321138 B1 | 4/2006 |
| RU | 2318500 C2 | 3/2008 |
| WO | 99/26582 | 6/1999 |
| WO | 2004/014927 | 2/2004 |
| WO | 2006/005759 | 1/2006 |
| WO | 2007/046729 A1 | 4/2007 |
| WO | 2008/048134 A1 | 4/2008 |
| WO | 2009/005386 A1 | 1/2009 |
| WO | 2009/158348 A1 | 12/2009 |

OTHER PUBLICATIONS

Denusiv (Kinetics and Catalysis, 2006, vol. 47, No. 5, pp. 662-671).*
Coulter et al (Free Radical Biology & Medicine, vol. 28, No. 10, pp. 1547-1554, 2000).*
PubChem compound CID 388445; Mar. 26, 2005 [retrieved from http://pubchem.ncbi.nlm.nih.gov/summary/summary.cgi?cid=38845&loc=ec_rcs on Jul. 31, 2012] whole doc (4 pages).
International Search Report and Written Opinion of the International Searching Authority, PCT/US12/40711, Aug. 20, 2012 (9 pages).
Popova et al., "MitoQ induced miofibroblast differentiation of human fibroblasts," Biochimica et Biophysica Acta, No. Suppl. S: 433-434 (2006).
Reddy PH, "Mitochondrial oxidative damage in aging and Alzheimer's disease: implications for mitochondrially targeted antioxidant therapeutics," J Biomedicine and Biotech, 2006: 1-13.
Sheu et al., "Targeting antioxidants to mitochondria: a new therapeutic direction," Biochimica et Biophysica Acta, 1762(2): 256-265 (2006).
PCT International Preliminary Report on Patentability for International Application No. PCT/RU2007/000043, issued Aug. 4, 2009.
PCT International Search Report for PCT Application No. PCT/RU2007/000043, mailed Nov. 1, 2007, 2 pages.
PCT Written Opinion of the International Searching Authority for PCT Application No. PCT/RU2006/00546, mailed Oct. 11, 2007, 6 pages.
Adlam et al. (2005) "Targeting an antioxidant to mitochondria decreases cardiac ischemia-reperfusion injury," FASEB J., 19:1088-1095.
Agapova et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).
Anisimov (2007) "Molecular and Physiological Mechanisms of Aging," Antioksidanty, Nov. 27, 2007, [on line] http://imquest.alfaspace.net/BOOK/MFMA/mfma_3_9_2.htm?embedded=yes translated from Russian to English.
Antonenko et al. (2008) "Mitochondria-Targeted Plastoquinone Derivatives as Tools to Interrupt Execution of the Aging Program. 1. Cationic Plastoquinone Derivatives: Sythesis and in vitro Studies," Biochemistry, 73(12)1273-1287.
Antonenko et al. (2008) "Protective effects of mitochondria-targeted antioxidant SkQ in aqueous and lipid membrane environments," J. Membr. Biol., 222:141-149.
Becker (2004) "New concepts in reactive oxygen species and cardiovascular reperfusion physiology" Cardiovascular Research, 61:461-470.
Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep., 26:231-243.

Brand et al. (1992) "The mechanism of the increase in mitochondrial proton permeability induced by thyroid hormones," Eur. J. Biochem. 206:775-781.
Doughan et al. (2007) "Original Research Communication: Mitochondrial Redox Cycling of Mitoquinone Leads to superoxide Production and Cellular Apoptosis," Antioxid. & Redox Signal., 9(11):1825-1836.
Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005 : 1-18, Invest. Ophthalmol. Vis. Sci., 46(9):3426-3434.
Green et al. (2004) "Prevention of Mitochondrial Oxidative Damage as a Therapeutic Strategy in Diabetes," Diabetes, 53(1):S110-S118.
Hansford et al. (1997) "Dependence of H2O2 formation by rat heart mitochondria on substrate availability and donor age," J. Bioenerg. Biomem. 29(1):89-95.
Havens et al. (2006) "Regulation of Late G1/S Phase Transition and APCCdh1 by Reactive Oxygen Species," Mol. Cell. Biol., 26(12):4701-4711.
Holloszy (1998) "Longevity of exercising male rats: effect of an antioxidant supplemented diet," Mechanisms of Ageing and Development, 100:211-219.
King et al. (2004) "Mitochondria-derived reactive oxygen species mediate blue light-induced death of retinal pigment epithelial cells," Photochem and Photobiol., 79(5):470-475.
Kirschner et al. (1994) "Role of iron and oxygen-derived free radicals in ischemia-reperfusion injury" J. Am. Coll. Surg., 179:103-117.
Li et al. (2000) "Skeletal muscle respiratory uncoupling prevents diet-induced obesity and insulin resistance in mice," Nat. Med. 6(10):1115-1120.
Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.
Longo et al. (2005) "Programmed and altruistic ageing," Nature Reviews Genetics, 6:866-872.
Lou et al. (2007) "Mitochondrial Uncouplers With an Extraordinary Dynamic Range," Biochem. J., 407:129-140.
Mecocci et al. (2000) "Plasma antioxidants and longevity: a study on healthy centenarians," Free Radical Biology and Medicine, 28(8):1243-1248.
Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73(12):1317-1328.
Orr et al. (2003) "Effects of overexpression of copper-zinc and manganese superoxide dismutases, catalase, and thioredoxin reductase genes on longevity in Drosophila melanogaster," J. Biol. Chem., 278(29):26418-26422.
Papp et al. (1999) "Glutathione status in retinopathy of prematurity," Free Radic. Biol. & Med., 27(7-8):738-743.
Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.
Petrosillo et al. (2006) "Protective effect of melatonin against mitochondrial dysfunction associated with cardiac ischemia-reperfusion: role of cardiolipin," FASEB J., 20:269-276.
Skulachev (2007) "A Biochemical Approach to the Problem of Aging: 'Megaproject' on Membrane-Penetrating Ions. The First Results and Prospects," Biochem. (Moscow), 72(12):1385-1396.
Popova et al. (2010) "Scavenging of Reactive Oxygen Species in Mitochondria Induces Myofibroblast Differentiation," Antiox. & Redox. Signal., 13(9):1297-1307.
Pozniakovsky et al. (2005) "Role of mitochondria in the pheromone- and amiodarone-induced programmed death of yeast,"J. Cell Biol., 168(2):257-269.
Sundaresan et al. (1995) "Requirement for Generation of H2O2 for Platelet-Derived Growth Factor Signal Transduction," Science, 270:296-299.
Reliene et al. (2007) "Antioxidants suppress lymphoma and increase longevity in atm-deficient mice," J. Nutrition, 137:229S-232S.

(56) References Cited

OTHER PUBLICATIONS

Riess et al. (2004) "Reduced reactive O2 species formation and preserved mitochondrial NADH and [Ca2+] levels during short-term 17° C. ischemia in intact hearts," Cardiovascular Research, 61:580-590.
Yildirim et al. (2005) "Role of oxidative stress enzymes in open-angle glaucoma," Eye, 19:580-583.
Zweier et al. (1987) "Direct measurement of free radical generation following reperfusion of ischemic myocardium," PNAS USA, 84:1404-1407.
Sidorova et al. (2004) "Transcriptional activation of cytochrome P450 1A1 with alpha-tocopherol," Bull Exp. Bio. Med., 138(3):233-236.
Skulachev (2005) "Critical Review: How to Clean the Dirtiest Place in the Cell: Cationic Antioxidants as Intramitochondrial ROS Scavengers," IUBMB Life, 57(4/5):305-310.
Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.
Tompkins et al. (2006) "Mitochondrial dysfunction in cardiac ischemia-reperfusion injury: ROS from complex I, without inhibition," Biochim. Biophys. Acta. 1762:223-231.
Starkov et al. (1997) "6-ketocholestanol is a recoupler for mitochondria, chromatophores and cytochrome oxidase proteoliposomes," Biochim. Biophys. Acta. 1318:159-172.
International Search Report dated Dec. 20, 2007 and International Preliminary Report on Patentability dated Nov. 10, 2009, PCT/RU2007/000171 (16 pages).
International Search Report and Written Opinion, PCT/RU2006/000547, dated Jul. 5, 2007 (7 pages).
International Search Report and Written Opinion, PCT/RU2006/000394, dated Nov. 2, 2006 (6 pages).
International Search Report, PCT/RU2008/000706, Aug. 13, 2009 (3 pages).
International Search Report and Written Opinion of the International Searching Authority, PCT/RU2007/000355, Mar. 27, 2008 (10 pages).
PCT International Search Report mailed Nov. 1, 2007 and International Preliminary Report on Patentability issued Aug. 4, 2009 for PCT Application No. PCT/RU2007/000043, 9 pages.
International Search Report and Written Opinion of the International Searching Authority, PCT/RU2009/000295, Feb. 25, 2010, 7 pages.
PCT International Search Report and Written Opinion of the International Searching Authority for PCT Application No. PCT/RU2006/000546, mailed Jul. 5, 2007, 14 pages.
International Search Report and Written Opinion of the International Searching Authority, PCT/RU2007/000044, Nov. 1, 2007, 9 pages.
International Search Report and Written Opinion, PCT/RU2009/000621, dated Aug. 12, 2010 (12 pages).

\* cited by examiner

PHARMACEUTICAL AND COSMETIC COMPOSITIONS FOR ACCELERATED HEALING OF WOUNDS AND OTHER SURFACE DAMAGES

BACKGROUND OF THE INVENTION

Wound topical treatment with bondages is one of main methods of first-aid and wound complex treatment, and, in some cases is the only possible treatment (e.g. when patient has concomitant disease, in case of extensive injuries or contraindications to surgery, etc).

Invention of bioactive bondages (dressings) played a significant role in development of modern topical treatment techniques. Bioactive bondages are based on natural, artificial or synthetic materials; contain medical or bioactive agents; actively influence on wound tissues and wound process due to some features of the bondage basis. Basic research of wound process pathogenesis has shown that a drug couldn't be universal and unequivocally effective at treatment of wounds of a various etiology at certain healing stages.

According to studies biology of wound healing biology, it was proved that medical tactics and means should be defined by a phase of wound healing process.

According to classification there are three main stages of wound healing process:

The first stage of an inflammation characterized by presence of edema, rich separation, invasion of microbes, necrosis development, frustration of microcirculation and metabolic disorder;

The second stage of regeneration, formation and maturing granulation tissue;

The third stage of epithelium development and cicatrix reorganization.

Modern methodology of topical wound treatment is based on special features of each stage and conception of necessity of directed and differentiated influence of bondage on wound process. Accordingly such treatment must be based on principles that imply an availability of various medical dressing's types with programmed effect on wound process. Additionally, it is necessary for practicing surgeon to have various bondages and corresponding information about its effect on wound healing.

Dressings for wounds on stage I (stage of inflammation) have to be as following: to have a sorption capacity; to provide outflow of wound separations and microflora from wound fundus; to have anti-inflammatory, antiedemic, antibacterial and proteoclastic effects; to promote normalization of microcirculation and regeneration processes.

Dressings for wounds on stage II s have to provide corresponding conditions for normal cell proliferation in regenerating tissue, positively affect epithelial cell angiogenesis, mobility On the third stage of wound process dressings have to provide corresponding conditions for normal cell proliferation in regenerating tissue and epithelium, prevent wound recontamination and create conditions for precaution of keloid cicatrix formation.

Modern wounds are in most cases characterized by a chronic process due to weakness of the immune status and with concomitant diseases. This pathology is characterized by duration of time and a long course of wound process, predisposition to retrocession and often leads to partial or full disability. Treatment of this category of patients becomes a serious medical and social problem all over the world. For their treatment a complex of biologically active dressings including ones that stimulate wound process run has been created.

The important role in making of a spectrum of biologically active dressing played a development of wound dressings with antioxidant activity that allows to arrest inflammatory processes at early of wound process and to set up conditions for a normal regeneration run. However application of traditional antioxidants is associated with certain difficulties connected with undirected localization of these substances in a cell and in whole organism.

DESCRIPTION OF THE INVENTION

The invention is based on a principle, which implies concentration of biologically active substances in mitochondria of a living cell using electrochemical potential energy of hydrogen ions and Skulachev ions. Such approach has unexpectedly allowed to lower significantly a dosage of used biologically active substances and to affect directly and efficiently on mitochondria—key elements of the major intracellular processes. That gives a possibility to decrease in many times probability and scale of undesirable side effects.

Thus one of the aspects of the present invention is a method of acting upon the organism with biologically active substances targeted into mitochondria by use of electrochemical potential energy of hydrogen ions.

In general, such a compound can be described by the following structure (I):

(structure I)

wherein A—effecter—antioxidant of structure:

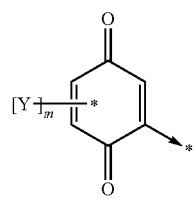

and/or reduced form thereof wherein m is an integer from 1 to 3; each Y is independently selected from the group consisting of: lower alkyl, lower alkoxy; or two adjacent Y groups, together with carbon atoms to which they are attached to form the following structure:

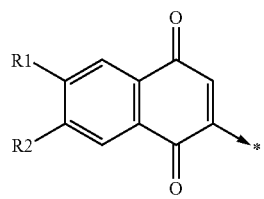

and/or reduced form thereof wherein R1 и R2 may be the same or different and are each independently lower alkyl or lower alkoxy;

L—linker group, comprising:
a) straight or branched hydrocarbon chain optionally substituted with one or more substituents and optionally containing one or more double or triple bonds;
b) natural isoprene chain;
n is integer from 1 to 20;
B—comprising:
a) Skulachev-ion Sk:

Sk⁺Z⁻ where Sk is a lipophilic cation, Z is a pharmacologically acceptable anion;
b) charged hydrophobic peptide containing 1-20 amino acid residues;
with proviso that in compound of structure (I) A is neither ubiquinone (e.g. 2-methyl-4,5-dimethoxy-3,6-dioxo-1,4-cyclohexadienyl) nor tocopherol or mimetic of superoxide dismutase or ebselen; with L—neither divalent decyl nor divalent pentyl or divalent propyl radical; and with B is triphenylphosphonium cation; including solvates, isomers or prodrugs thereof.

A further aspect of the present invention is a pharmaceutical composition for bioactive substance targeted transport into cell mitochondria comprising a compound of structure (II), wherein A—plastoquinone of structure:

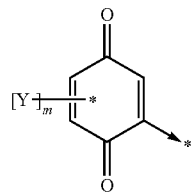

wherein Y—methyl, m=2;
L—linker group, comprising:
a) straight or branched hydrocarbon chain optionally substituted with one or more substituents and optionally containing one or more double or triple bonds;
b) natural isoprene chain;
n is integer from 1 to 20;
B—comprising:
a) Skulachev-ion Sk:

Sk⁺Z⁻ where Sk is a lipophilic cation, Z is a pharmacologically acceptable anion;
b) charged hydrophobic peptide containing 1-20 amino acid residues;
with proviso that in compound of structure (I) A is neither ubiquinone (e.g. 2-methyl-4,5-dimethoxy-3,6-dioxo-1,4-cyclohexadienyl) nor tocopherol or mimetic of superoxide dismutase or ebselen; with L—neither divalent decyl nor divalent pentyl or divalent propyl radical; and with B is triphenylphosphonium cation; including solvates, isomers or prodrugs thereof.

A further aspect of the present invention is a pharmaceutical composition for acceleration of wound and other body surface injuries healing processes using mitochondria-targeted antioxidants comprising a compound of structure (I)—SkQ1:

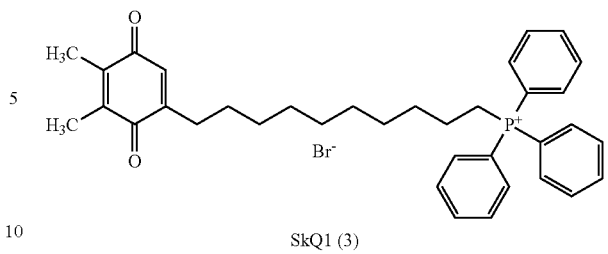

SkQ1 (3)

or analogous compositions (including SkQ1, SkQR1 and other mitochondria-targeted antioxidants).

According to this aspect of the invention the following is proposed:
Application of mitochondria-targeted antioxidants for helping of combustion recovery, wound and surgical suture healing.
Application of mitochondria-targeted antioxidants for amending of ulcer healing, including nutritional ulcers and diabetic wounds and ulcers.
Application of mitochondria-targeted antioxidants as anti-inflammatory agent
Application of mitochondria-targeted antioxidants during surgery to protect healthy tissues from being damaged.
Application of mitochondria-targeted antioxidants in transplantology for preventing of tissue rejection and saving of transplantological material.

A further aspect of the present invention is a pharmaceutical composition for acceleration of healing processes of wound and other body surface injuries comprises therapeutically or prophylactically effective amount of a compound of Structure (I) and at least one pharmacologically acceptable solvent or carrier. A pharmacologically acceptable solvent or carrier may present filler, a diluent (solvent) or their mixture. "Therapeutically effective" amount of a compound is an amount of a compound of Structure (I) that causes desired biological or medical response in a patient treated by a physician or veterinary doctor. "Prophylactically effective" amount of a compound is amount of a compound of Structure (I) that prevents or suppresses the disease, or relieves progress of the disease in a patient suffering from a medical state that is tried to be prevented, suppressed or relieved by a physician or veterinary doctor.

In one of the aspects of the present invention a human is a patient.

"Wounds and other surface injuries/damages" include but not limited by: wounds, connected to injuries of dermal epithelium, corneal epithelium, gastrointestinal tract surface, lung epithelium, liver blood vessel interface, blood vessel of metra, vaginal opening, urethra and respiratory passages. Present invention also provides therapy of wounds and other body surface injuries, connected to long-lasted epithelial defects and relapsing epithelial anabrosises, such as: surgical wounds, excision wounds, vesications, ulcers, other injuries, scratches, avulsive wounds, cuts, sordid wounds, furunculus and thermal or corrosive burns. Such wounds can be caused by both mechanical damage and other deseases, such as: diabetes, corneal dystrophy, uremia, luck of nutrition, vitamin deficit, obesity, infection, immunodeficit or complications, connected with systematical use of steroids, radiotherapy, nonsteroidal anti-inflammatory drugs and anticancer drugs.

Composition of Structure (I) can be used for acceleration of healing processes of wound and other body surface injuries regardless its causes.

A further aspect of the present invention is a method of preparation of composition, which can be used in cosmetology to improve skin condition, skin rejuvenation, and precaution of skin aging-related changes and for therapy including chronological aging, photoaging, skin damages, caused by sun light or by ultraviolet. Also the aspect of the present invention is a method of preparation of composition for mending hair growth, prevention of hair loss, and hair restoration.

Administration of pharmaceutical and cosmetological compositions, related to present invention, for treatment of human and other mammals comprises percutaneous, intradermal, oral, rectal, parenteral, intracisternal, intravaginal, intraperitoneal, buccal, per ocular or nasal. Prescription can be both therapeutic and for prophylaxis. Soluble pharmaceutical composition for peroral administration includes but not limited by: pharmacologically acceptable emulsions, microemulsions, solvents, suspensions, surups and elixirs. Solid pharmaceutical composition for peoral administration includes but not limited by: capsules, tablets, pellets, pulvis or granules. Pharmaceutical composition for percutaneous or intradermain administration includes but not limited by: unctures, pastas, creams, washes, gels, pulvis, liquids, sprays, inspirators or bondages. Pharmaceutical compositions for injections include but not limited by: sterile water or oil suspensions. Pharmaceutical compositions for intravaginal and rectal administration are preferably in suppository form.

Pharmaceutical compositions for prophylaxis application can be used for therapy of potential wound's origins or initial wound surfaces, such as: contact lenses, liquids for contact lens cleaning and washing, containers for contact lens transport and storage, eye drops, solutions for surgical wash, hear drops, eye bondages and cosmetic products for eye areas.

A further aspect of the present invention is ophthalmologic devices, surgical equipment, audiologic equipment and other products containing pharmaceutical compositions of current invention (e.g. gauze bandages and dressings or plasters).

When a compound of structure (I) is administered as a pharmaceutical composition, the compound of structure (I) should be mixed according to formula with a suitable amount of pharmacologically acceptable solvent or carrier so that to have the appropriate form for administration to a patient. The term "solvent" relates to diluent, auxiliary medicinal substance, filler or carrier which is mixed with the compound of structure (I) for administration to a patient. Liquors like water, and oils including petrolic, animal, vegetative and synthetic such as peanut oil, soybean oil, mineral oil and other similar oils can be used as said pharmacological carriers. Normal saline solution, acacia pitch, gelatin, starch, talc, keratin, colloid silver, urea etc can serve as said pharmacological solvents. Said composition can also include auxiliary substances, stabilizers, thickeners, lubricant and coloring agents.

The compounds and compositions of the present invention can be administered in the form of capsules, tablets, pills, pillets, granules, syrups, elixirs, solutions, suspensions, unctures, creams, sprays, emulsions, suppositories, retarded release substances, or in any other form suitable for administration to a patient.

A further aspect of present invention is application of compounds of Structure (I) and pharmaceutical compositions in form of creams, unctures or tablets for percutaneous or per oral administration.

A further aspect of present invention is a pharmaceutical composition that includes one or more additional therapeutic agent or compounds besides one of Structure (I). A list of "additional therapeutic agents" includes without limitations: growth factors, anti-inflammatory drugs, vasopressor agents and drugs, collagenase inhibitors, steroids, matrix metalloproteinase inhibitors, ascorbates, angiotensins II, angiotensins III, calreticulin, tetracycline, fibronectin, collage, thrombospondin, transforming growth factors (activin), keratocyte growth factors, fibroblast growth factors (including FGF-2 fibroblast growth factor), insulin-like growth factors, epidermal growth factors, hepatocyte growth factor and hyaluronic acid.

Therapeutically effective amount of a compound of Structure (I) required for treatment of a specific disease or symptom, depends on the nature of disease or symptom and a method of administration and should be determined at consultation with a physician in charge.

Preformed experimental work demonstrated compound of Structure (I) to be effective in treatment of said diseases and patient condition improvement if administered in compositions containing from 0.1 pmol to 300 µmol per 1 gram of the composition depending of particular case of the disease. For SkQ1 the efficient dosage is from 62 picograms to 185 milligrams per 1 gram of the composition.

An Example of Pharmaceutical and Cosmetic Compositions, Related to Present Invention Ointment-1

| | |
|---|---|
| Active compound (SkQ1) | 15 microgram |
| Silicone oil | 20 gram |
| White Vaseline | up to 100 gram |

Ointment-2

| | |
|---|---|
| Active compound (SkQ1) | 1.5 microgram |
| Cetostearyl alcohol | 14 gram |
| White Vaseline | 20 gram |
| Water (distilled) | up to 100 gram |

Cream for Percutaneous Administration-1

| | |
|---|---|
| Active compound (SkQ1) | 15 microgram |
| Olive oil | 5.0 gram |
| Cetyl alcohol | 2.0 gram |
| Stearic acid | 5.0 gram |
| Aliphatic acid glycerin ether | 12.0 gram |
| Tween 60 | 5.0 gram |
| Propyleneglycol | 5.0 gram |
| Propylparaben | 0.02 gram |
| Water (distilled) | up to 100 gram |

Cream for Percutaneous Administration-2

| | |
|---|---|
| Active compound (SkQ1) | 1.5 microgram |
| Beewax | 0.6 gram |
| Diisostearoyl polyglyceryl-3 dimer dilinoleate | 3.0 gram |
| Silicone oil | 0.4 gram |
| Oleyl oleate | 6.0 gram |
| Ethylhexyl palmitate | 5.0 gram |
| Isopropyl isostearate | 5.0 gram |
| Glycerol | 3.0 gram |
| Magnesium sulfate | 1.0 gram |
| Bisabolol | 0.5 gram |
| Propylparaben | 0.05 gram |
| Methylparabene | 0.15 gram |
| Water (distilled) | up to 100 gram |

Suppository

| Active compound (SkQ1) | 15 microgram |
|---|---|
| Witepsol ™ W-35 | 100.0 gram |

Film-coating (var. 1)

| Active compound (SkQ1) | 2 microgram |
|---|---|
| Chitine-based polymer | 100.0 gram |

Film-coating (var. 2)

| Active compound (SkQ1) | 2 microgram |
|---|---|
| Polyvinyl alcohol based polymer | 100.0 gram |

A further aspect of present invention is experimental data showed below; it confirms possibility of mitochondria-targeted antioxidants application (e.g. SkQ1 or SkQR1).

DETAILED DESCRIPTION OF THE INVENTION

Experimental Examples

1. Mitochondrial Antioxidant SkQ1 cause Human Fibroblasts to Differentiate into Myofibroblasts Myofibroblasts emerge as result of normal fibroblast differentiation and in comparison to them have bigger size, better adherence to the substrate (in vivo to extracellular matrix, in vitro to plastic), different cytoskeleton structure and contractive activity.

Due to ability to contract and brace wound edges myofibroblasts play crucial role in wounds (both flesh and interior) healing.

Experimental data listed below clearly demonstrates that human subdermal fibroblasts incubation with antioxidant SkQ1 leads to stable differentiation of noticeable part of cells into myofibroblasts.

Studies of human subdermal diploid fibroblasts, treated with SkQ1 (added to culture medium up to 20 nM concentration) reveals significant changes in cell morphology and surface enlargement. More detailed analyses demonstrates that after SkQ1 treatment an initial population divides in two: in one average square does not differ from one in control group, the other group consists of cells with average square from 3 to 5 times bigger than corresponding values for control group.

Figure 1:
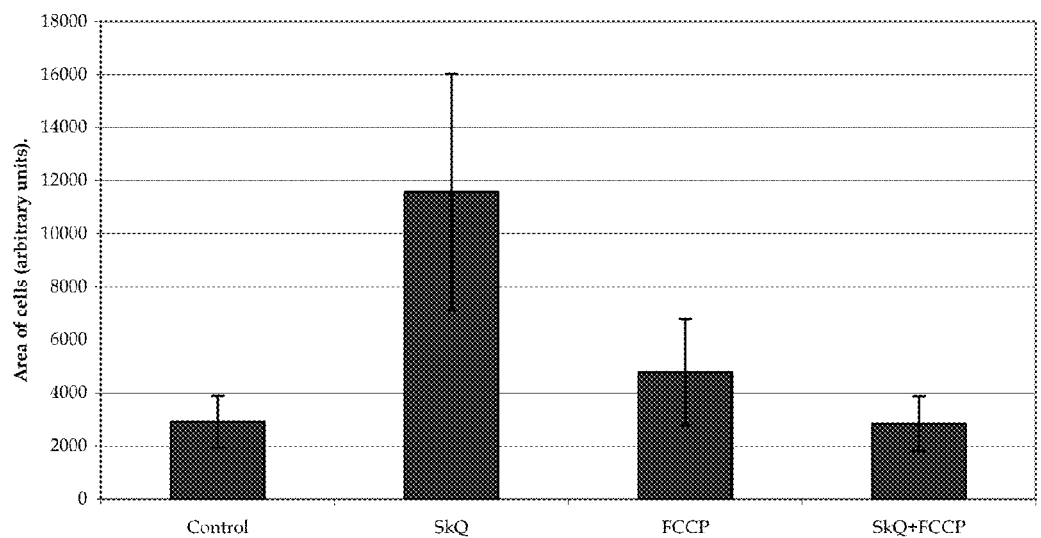
FIG. 1 shows average fibroblast square/surface enlargement, caused by incubation with SkQ1.
Figure 2:
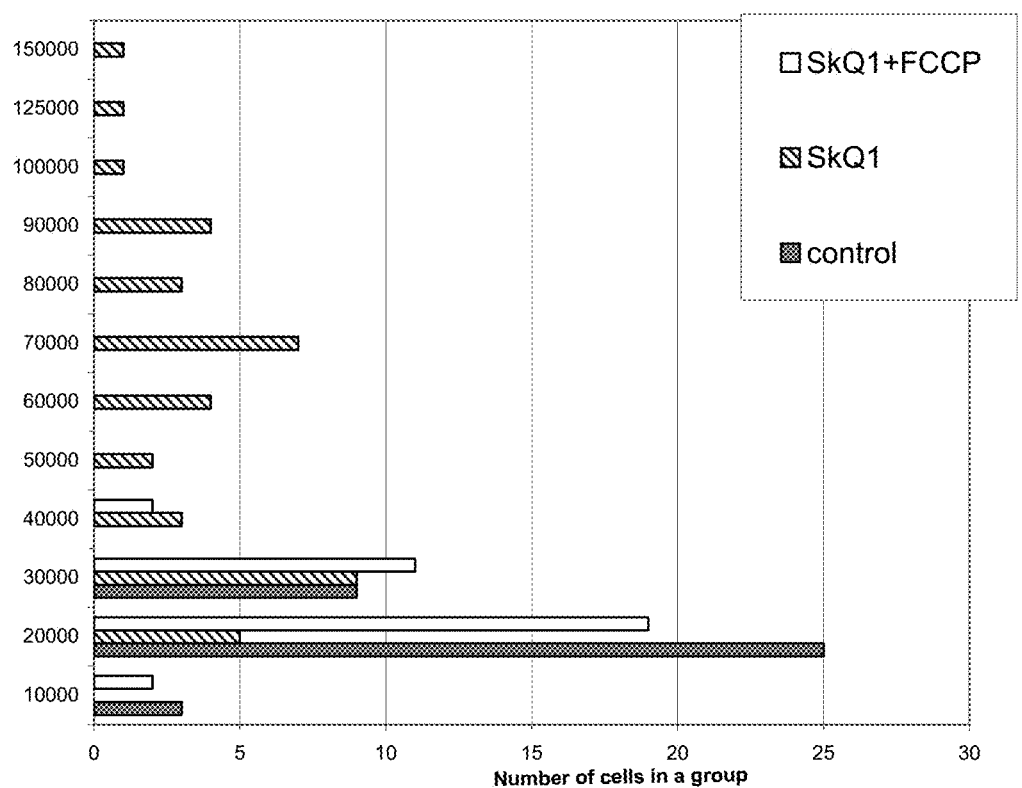
FIG. 2 shows fibroblast incubation with SkQ1 to cause emerging of cells with larger square/surface. Cell surface is given in relevant units.

Average square value increases more then two-three fold, but this does not reflects the whole changes. Data on cell size distribution (FIG. 2) demonstrates emergence of significant group of cells with average square increasing control value 5-6 fold.

This data clearly demonstrates that morphology of fibroblasts treated with SkQ1 corresponds to one of myofibroblasts.

Main myofibroblast marker is unstriped muscle actin form, which mediates its contraction activity and almost never can be found in normal fibroblasts. IF staining of unstriped muscle actin form demonstrates heavy increase in its consistence in "giant" cells emerging after SkQ1 treatment in comparison to consistence of unstriped muscle actin form in normal fibroblasts.

Figure 3:
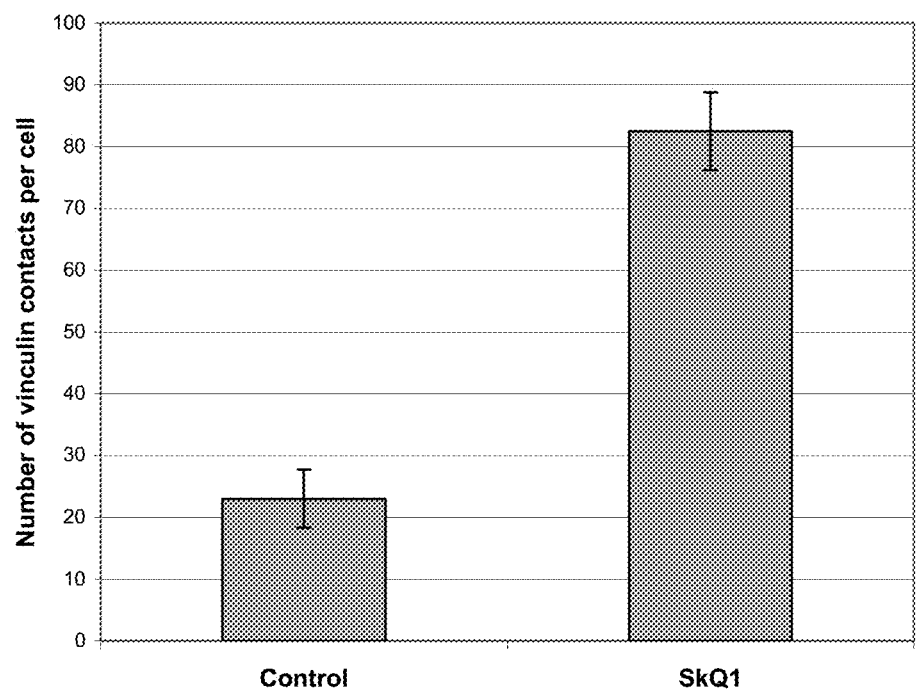
FIG. 3 shows increase of vinculin-containing contact number per cell, caused by human fibroblast preincubation with SkQ1.

Better adherence to the substrate is also a characteristic feature of myofibroblasts, it promotes its movement into wound and brace of wound edges. In our experiments we estimated number of tight contacts between cell and substrate, containing special focal adhesion protein vinculin. Comparison of control cells with cells, treated with SkQ1, is shown on FIG. 3 and demonstrates increase of number of contacts per cell, what reflects an increase in cell adherence rate.

Data given above convincingly demonstrates that human fibroblast treatment with mitochondria-targeted antioxidants, for example SkQ1, leads to transformation of significant part of fibroblasts into myofibroblasts, what should accelerate wound healing and regeneration of human or animal damaged tissues. It is important to notice that short incubation with SkQ1 for 1-2 hours is enough for induction of this transformation, and further a population of myofibroblasts is supported in a media without SkQ1 for at least 4-6 weeks.

2. SkQ1 causes Increase in Expression of Specific Proteins, Related to Wound Accelerated Healing In our experiments we demonstrated SkQ1 to cause active cell skeleton reorganization with stress-fibril enhancement. It points to contraction activity and cell movement enhancement. This was also proved by analysis of amount of non-muscle myosin bonded to actinic fibrils. This was done by IF staining of actin and myosin in fibroblast stress-fibrils, treated with SkQ1 and from control group.

Further on we analyzed a consistence of main extracellular matrix protein fibronectin in fibroblast culture, treated with SkQ1. By means of IF staining we demonstrated a significant increase of fibronectin's level both in monolayer areas and in cell migration zone. Fibronectinic matrix forms as a result of both cell secretion and reorganization of matrix components present in culture in formation of serum. Fibronectin produced by fibroblasts has certain structural alterity that gives a possibility to construct selective antibodies. Using these antibodies we managed to demonstrate that intracellular expression of fibronectin raises in presence of SkQ1, what also reflects SkQ1 ability to accelerate healing of wounds of very different kind.

3. Acceleration of Wound Healing Demonstrated using Human Fibroblast Monolayer Model Human fibroblast monolayer damage—is a model of wound in vitro, as fibroblasts are basement of connective tissue, which structure falls with any injury or damage. It is known that fibroblasts are one of the first to enter wounded area that considerably determines its healing.

Figure 4:
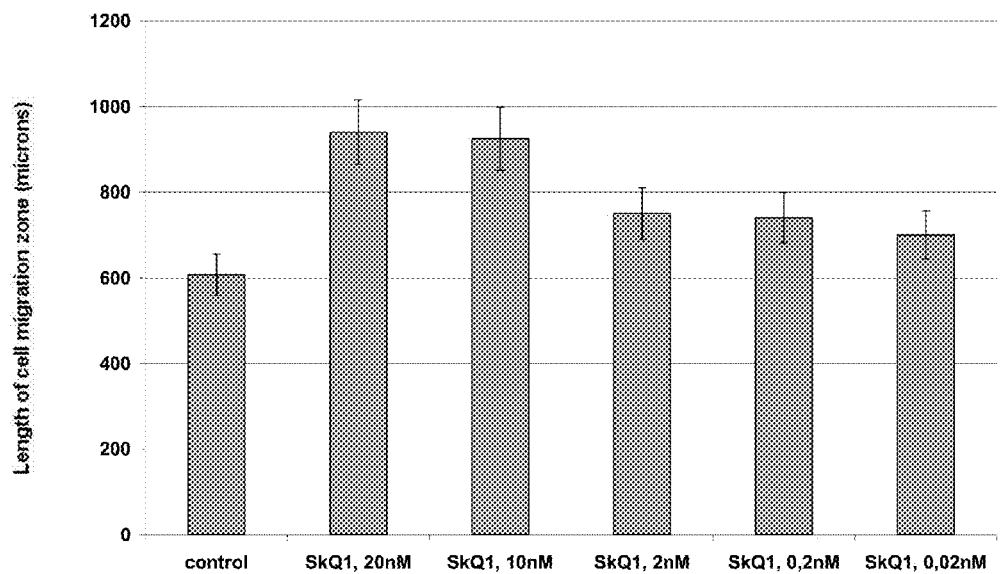
FIG. 4 shows different SkQ1 concentration effect (1-day-incubation in presence of antioxidant and 17-day-incubation without it) on length of human fibroblast migration into wound zone during 1 day.

Fibroblast monolayer was damaged with sterile scalpel; as a result a 2000 micron wide distant break appeared. Ability of fibroblasts to heal the wound was estimated by length of cell migration zone, appeared during certain time period (1 day) inside the wound. Cell migration zone length depends directly on healing speed of artificially given wound. Results of several different SkQ1 concentrations test are shown on FIG. 4. Just like in studies of morphology, it can be seen that short period incubation with SkQ1 caused effect, which continued for a long time even without SkQ1.

Figure 5:
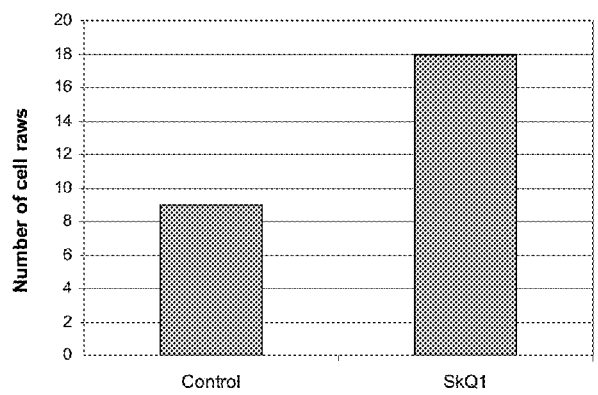
FIG. 5 shows quantitative evaluation of SkQ1 influence on human fibroblast migration to the wound speed. Number of rows "entered" to the wound in 24 hours was evaluated.

Injury healing acceleration can also be observed from counting number of cell rows, entered to the wound in 24 hours (FIG. 5).

Obtained results convincingly demonstrates that mitochondia-targeted antioxidants, e.g. SkQ1, can stimulate fibroblast accumulation in the wound and their transformation into myofibroblasts. Both these effects should promote healing of different kind of wounds.

4. Acceleration of Epithelial Layer Movement into the Wound In Vitro Mediated by SkQ1.

Along with fibroblast movement and contraction, in wound healing a formation plays an important role of new epithelial layers in the wound—so called reepithalialization. Study on this process in vitro was carried out using LAR epithelial cell line. Treatment with SkQ1 didn't cause significant morphological changes. Ability of cell to form tight "islands" and single epithelial layer also weren't disturbed. Studies on expression of intracellular contact protein E-cadherin specific for epithelium confirmed epithelial structure stability in presence of SkQ1. In the same time consistence of actinic stress-fibrils in the cells significantly raised, what reflected potential enhancement in movement. This effect was studied in vitro using the same mode that was used in fibroblast studies. Just like with fibroblasts, SkQ1 significantly accelerates cell movement into the wound. Unlike fibroblasts, epithelial cells moved into the wound in a single layer with all characteristic morphology and intracellular contacts.

SkQ1 effect also continued long after drug withdrawal just like in case with fibroblasts.

Obtained data point out, that mitochondia-targeted antioxidants, e.g. SkQ1, can stimulate wound reepithelialisation and promote wound healing on the corresponding stage.

5. Medico-Experimental Study of Biologically Active Wound Dressing with Immobilized Mitochondria Targeted Antioxidant SkQ-1.

Using this experimental example we demonstrated that application of certain concentrations of SkQ1 (e.g. SkQ1 immobilized on polymeric-based wound dressing) can significantly accelerate wound healing and positively influence on whole wound process.

Obtained Results

1. Medical and Biological Description of Wound Healing

As a base for immobilization of mitochondria-targeted antioxidant SkQ-1 a film wound coverings, based on complex of polyvinyl alcohol and animal polysaccharide (chitosan), were used.

Flowing was as a starting material:
chitosan, extracted from krill
polyvinyl alcohol of low-molecular weight (medical).

Forming of wound covering based on PVA and chitosan was preformed by application on mirrored metallic base sheet. Crosslinking agent was introduced to polymer solution. Drying was preformed at room temperature.

Antioxidant SkQ1 were introduced into biosynthetic coverings on the stage of polymer solution formation. Introducing of biologically active ingredients into polymeric complexes at the stage of its formation is technologically justified and effective, as it provides minimal possibility of drug inactivation and best conditions for its homogeneous distribution in the structure. Antioxidant SkQ1 were introduced in concentration 0.02 microgram per gram of polymer.

Study of specific activities of SkQ1 containing dressings was carried out on animals—white rats. Biomedical research on SkQ1 containing dressings was performed in experiment with treatment of full-thickness skin wound with aseptic inflammation. Experiment was conducted on 20 white linear outbreed rats with weighed 150-200 gram. At the first stages full-thickness wounds were formed in rats' interscapular region. Only apyetous aseptic wounds were modeled. For wound formation on rats back after depilation under ether anaesthesia a full-thickness area up to 2 cm in diameter was incised down to underlying fascia. After that a treatment started using dressings of different composition, each containing SkQ1 antioxidant. Rats were then divided in groups according to type of dressings:

1—bulky dressing (control group)
2—film covering with SkQ1 immobilized in concentration 0.02 microgram per gram of polymer.

Wound process control was carried out by virtue of:
1) Data from clinical observation of wound process:
Wound edge or wound tissue edema occurrence in wound area, hyperemia, manipulation sickliness;
Necrotic detritus and wound effluent occurrence;
Time of wound clearance from purulo-necrotic detritus, time of inflammation arrest, granulation tissue occurrence, its maturity degree, time of reepithelialization.
2) Unbiased wound process estimation criteria
Wound defect square planimetric estimation method.
Dynamic morphological analysis of experimental animal's wound probes Original wounds were characterized by mild consecutive hemorrhage and small edema characteristically for primary traumatic injury. Wounds were rebondaged every day. After dressing removal wounds were cleansed with antiseptic solutions. Biopsy probes were taken from each pair of rats for morphological analysis.

According to clinical observation data, on the first day after bondaging in trial group, where animals were treated with polysaccharidic films containing SkQ1 in concentration 0.02 microgram per gram of polymer, only insignificant amount of effluent was registered, wound fundus was clear, faintly pink, with good vascularization, without signs of inflammation. Wound edges were tightly fixed. Bondage removed from wound without difficulties. In control group, where wounds were treated with bulky dressings, dressing adhesion to the wound were registered, but removal didn't cause consecutive hemorrhage. Wound fudnus was faintly pink, without edema or inflammation expressed.

On the second day after bondaging in trial group, where animals were treated with polysaccharidic films containing SkQ1-0.02, wounds were moist with gray scurf areas on the fundus. Wound edges were tightly fixed with features of expressed edge epithelialisation. Undressing didn't lead to consecutive hemorrhage. 14.8% wound contraction was registered. In control group after bulky bondage removal wound slightly bled, wound fundus demonstrated fibrin elements and contained no effluent. Only 0.7% wound contraction was registered.

On the third day in control group—wound fundus was covered with yellow pellicle, of faintly pink colour, with granulation tissue. Films did not lysed and almost didn't swell, it was removed without damaging underlying tissues. 20.2% wound contraction was registered in comparison to $2^{nd}$ day. In control group after bulky bondage removal wound slightly bled, wound fundus was faintly pink, demonstrated fibrin elements and contained no effluent. 23.6% wound contraction was registered in comparison to $2^{nd}$ day.

On the second day after bondaging in trial group, where animals were treated with polysaccharidic films containing SkQ1-0.02, wound fundus was faintly pink, covered with granulation tissue without sings of edema or inflammation. Films didn't swell and were removed without damaging underlying tissues. 17.5% wound contraction was registered in comparison to $3^{rd}$ day. In control group after bulky bondage removal wound remains didn't change significantly from last checkpoint: wound fundus was faintly pink, demonstrated fibrin elements and contained no effluent. 5.6% wound contraction was registered in comparison to $3^{rd}$ day.

On the $7^{th}$ day a significant decrease in wound size were observed in test group, wound fundus (bottom) was dry and covered with faintly pink granulation tissue, wounds demonstrated evident limbic epithelialization. 42.4% wound contraction was registered in comparison to $4^{th}$ day. In control group after removal of a gauze bandage wound did not bleed, wound fundus contained small amount of wound effluent (coagulable lymph), and was faintly pink with gray scurf. 8.9% wound contraction was registered in comparison to $4^{th}$ day.

According to clinical observation of wound process passage in wounds treated with bondages with immobilized SkQ1, polysaccharidic films with 0.02 µg/g SkQ1 appeared to be most efficient in full-thickness skin wounds treatment, inflammatory process arresting and wound contraction.

2. Cytological and Morphological Studies of SkQ1 Effect on Wound Healing

Along with biomedical description of wound healing morphological analysis of tissues samples from wounds, treated with dressing, containing SkQ1 in different concentrations was performed.

Research Methods

Light microscopy research of 350 semifine sections was performed. Samples were taken on $1^{st}$, $2^{nd}$, $3^{rd}$, $4^{th}$ and $7^{th}$ day. $1^{st}$ and $2^{nd}$ days corresponded to inflammatory stage, $3^{rd}$, $4^{th}$ and $7^{th}$ days corresponded to granulation tissue forming and maturing stages. Each day number of fibroblasts and blood vessels was counted. Counting were made by studying of 30 random 100 mm$^2$ visual fields from each sample using ×1000 immersion zoom, after that mean values were taken.

Obtained Results

On the $1^{st}$ day more or less expressed inflammatory reaction was observed in each group of animals. Observed increased intracellular distances reflected on progress of edema. In wound area among changed blood vessels of medium and large size and adipocytes the single fibroblasts and capillaries appeared.

In test groups the wounds were treated with SkQ1 in different concentrations, and inflammatory sings were not that expressed as in control group 1. Neither leukocyte marginal position nor tissue paranasal hydration was observed. Wound surfaces were covered with pseudomembrane with segmental leukocytes and cell debris. In wound upper layers a huge number of macrophages and some segmental leukocytes were observed. New fibroblasts and single minute vessels appeared.

On the $1^{st}$ day of a treatment the biggest number of fibroblasts was registered in group bondaged with dressings contained SkQ1 in lowest concentration (0.02 microgram per gram of polymer)—6.93. Fibroblast number decrease correlated with increase in antioxidant concentration in a polymer (see table 1).

In test groups on the $1^{st}$ day both young fibroblasts with big nucleus and organelle-poor cytoplasm and functionally active fibroblasts with well-marked cytoplasm, big mitochondria and big number of polyribosomes were found in the wound.

The biggest number of minute vessels was also registered in group, treated with dressings containing SkQ1 in lowest concentration (see table 2).

Due to this on the $1^{st}$ day of a treatment condition of wounds, treated with SkQ1 was much better than in condition of ones in control group. Number of fibroblasts and small vessels was biggest in group, treated with dressing contained SkQ1 in minimal concentration (0.02 microgram per gram of polymer)

TABLE 1

Average number of fibroblasts in wounds treated with SkQ1.

| | Day of treatment | | | | |
|---|---|---|---|---|---|
| | 1 | 2 | 3 | 4 | 7 |
| Control | 0.15 | 0.21 | 8.6 | 12.73 | 19.6 |
| SkQ1 solution - 0.2 µg/g | 3.93 | 8.93 | 9.33 | 13.13 | 16.13 |
| Polymer with 0.2 µg/g SkQ1 | 5.13 | 5.46 | 19.75 | 22.1 | 10.6 |
| Polymer with 0.02 µg/g SkQ1 | 6.93 | 5.93 | 18.06 | 15.26 | 15.3 |
| Polymer with 2 µg/g SkQ1 | 3.66 | 7.53 | 16.73 | 27.06 | 44.4 |

TABLE 2

Average number of vessels in wound treated with SkQ1

| | Day of treatment | | | | |
|---|---|---|---|---|---|
| | 1 | 2 | 3 | 4 | 7 |
| Control | 0.11 | 0.09 | 1.4 | 1.66 | 1.8 |
| SkQ1 solution - 0.2 µg/g | 0.13 | 0.13 | 0.93 | 1.73 | 1.06 |
| Polymer with 0.2 µg/g SkQ1 | 0.06 | 0.06 | 2.0 | 1.6 | 0.66 |
| Polymer with 0.02 µg/g SkQ1 | 0.2 | 0.4 | 1.13 | 0.73 | 0.6 |
| Polymer with 2 µg/g SkQ1 | 0.06 | 0.4 | 0.93 | 2.26 | 2.0 |

On the $2^{nd}$ day in control group wounds inflammatory sings remained: tissue was edematic, destructive changes progressed. Neutrophilic infiltration and round cell element—lymphocyte, macrophage—migration could be registered. In test group active granulation tissue reorganization processes were registered. Along with lymphocytes macrophages new minute vessels appeared with nearby fibroblast accumulations. In group treated with SkQ in highest concentration number of fibroblasts increased more than twofold comparing to the previous checkpoint (see table 1). Number of blood vessels under such treatment increased more than six fold and reached number of vessels in group treated with SkQ1 in minimal concentration (see table 2).

On the $3^{rd}$ day of treatment in test group a wounds proliferative processes activation was registered, this led to significant increase in number of fibroblasts. Effect could be observed in groups treated with SkQ1 in different concentrations (see table 1). Increase of number of vessels was even more noticeable and also could be observed in all groups received SkQ1 (Table 2).

Fine structure analysis revealed fibroblasts in stage of mitosis, functionally active fibroblasts with big mitochondria, hypertrophied cytoplasmic granular reticulum with caverns filled with fine-grit containing. Monilated cells similar to fibroblasts and smooth muscle cells, with long arms were found. Cytoplasm of such cells contained a lot of polyribosomes, localized predominantly in cone cytoplasmic zone, and a lot of longwise oriented microfilaments among which tight bodies similar to ones in smooth muscle cells could be observed. Said features allowed identifying these cells as myofibroblasts—cells that plays a significant role in wound contraction and also actively synthesize intracellular matrix elements. Myofibroblasts formation after first collagen fibers accretion in granulation tissue allows assuming that certain number of fibroblasts transform into myofibraoblasts gaining contractive ability and orientating newly synthesized collagen fibers.

In granulation tissue a lot of minute vessels formed by 2-3 endothelial cells were found. Basal membrane, surrounded newly formed vessels, was not expressed. Granular cytoplasmic reticulum was represented by close profiles with lot of ribosomes and mitochondria. Along with small tight mitochondria some enlarged organelles with cleared matrix could be found. Such fine structure of endothelial cells reflects their high functional activity.

In such a way, at the $3^{rd}$ day of the treatment with SkQ1 expressed proliferative processes stimulation that led to significant increase of fibroblast an vessel number was registered. Functional activity of fibroblasts increased, myofibrobalsts appeared.

On the $4^{th}$ day granulation tissue in control group was less mature than one test groups—significant number of microphages was registered, among fibroblasts young one prevailed. In test group no significant changes in wound tissues could be observed comparing to last checkpoint. Granulation tissue was mature and was mainly represented by collagen-synthesizing fibroblasts with big nucleus, granular cytoplasmic reticulum covering almost all cytoplasm, big mitochondria and a lot of polyribosomes. Horizontal fibroblasts orientation outlined. Mitotic fibroblasts could be also found. Only single microphages were present. Number of fibroblasts in all groups almost didn't changed comparing to previous checkpoint. Maximum increase in number was observed under dressings with maximum SkQ1 concentration (see table 1). Number of vessels in this group doubled, but changed insignificantly in other groups (see table 2).

On the $7^{th}$ day wound defects in control group were filled with developing granulation tissue with lot of fibroblasts, vessels and microphages. In test groups regenerative tissue was much more mature; wound defects were filled with mature granulation tissue. In group received dressings with SkQ1 in maximal concentration young connective tissue was present by collagen fibers oriented longwise wound surface with monilated fibroblasts and fibrocytes. In this group maximal number of fibroblasts was registered, number of ones in other groups were much lower (see table 1). Number of vessels in all groups excluding control one decreased what reflected regenerative tissue maturity high rate. Vessels of minute type were oriented perpendicularly to wound surface.

CONCLUSION

Due to results of morphological analysis of tissue samples from wounds, treated with dressings, containing SkQ1 in various concentrations, we may assume that on the early stages of the treatment (1-2 days) the most efficient appeared to be dressings with SkQ1 in lowest concentration, and on later stages most efficient appear to be high concentrations of SkQ1. On early stages minimal doses of SkQ1 positively influence fibroblast proliferative processes leading to myofibroblasts appearance in granulation tissue, stimulate angiogenesis what allow restrict inflammatory stage and whole period of wound healing. On later stages (7 days) most positive effect comes with highest concentration of SkQ1. Possibly in practical application a change of concentrations may be useful on different wound healing stages.

The invention claimed is:

1. A method of treating a skin condition in a patient, the condition comprising chronological aging, photoaging, sunlight or UV light damage, burns, wounds, or sutures, the method comprising administering to the skin of the patient in need thereof a therapeutic amount of the pharmaceutical composition comprising a compound of formula (I):

wherein:
in the composition of Formula I, A is a plastoquinone of structure:

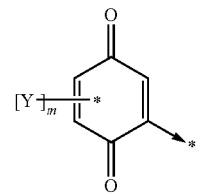

wherein:
Y is lower alkyl;
m is an integer from 2 to 3;
L is a linker group, comprising a hydrocarbon chain;
n is the number of carbon atoms in L, which is an integer from 1 to 20;
B is a targeting group comprising:
Sk⁺Z⁻, wherein:
Sk is a lipophilic cation; and
Z is a pharmacologically acceptable anion;
and isomers, and salts thereof; and a pharmaceutically acceptable carrier thereof; wherein the composition is targeted to and delivered into skin of the patient.

2. The method according to claim 1, wherein lower alkyl is methyl.

3. The method according to claim 1, wherein m is 2.

4. The method of claim 1, wherein the composition administered is SkQ1:

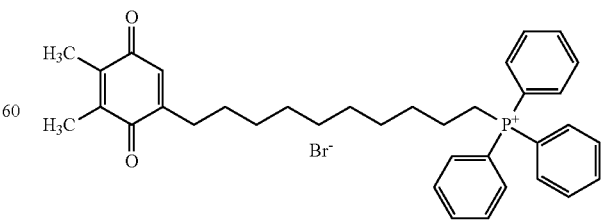

* * * * *